(12) United States Patent
Strebelle et al.

(10) Patent No.: US 7,320,779 B2
(45) Date of Patent: Jan. 22, 2008

(54) PROCESS FOR MANUFACTURING AN OXIRANE

(75) Inventors: Michel Strebelle, Brussels (BE); Jean-Pierre Catinat, Waudrez (BE)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 11/682,904

(22) Filed: Mar. 7, 2007

(65) Prior Publication Data

US 2007/0149790 A1 Jun. 28, 2007

Related U.S. Application Data

(62) Division of application No. 10/940,992, filed on Sep. 15, 2004, now Pat. No. 7,205,419, which is a division of application No. 10/182,776, filed as application No. PCT/EP01/00976 on Jan. 30, 2001, now Pat. No. 6,815,552.

(30) Foreign Application Priority Data

Feb. 2, 2000 (EP) ................... 00200344

(51) Int. Cl.
*B01J 8/22* (2006.01)
(52) U.S. Cl. ............... 422/187; 422/189; 549/531
(58) Field of Classification Search ............... 422/187, 422/189; 549/531
See application file for complete search history.

(56) References Cited

U.S. PATENT DOCUMENTS

| 6,518,441 B2 | 2/2003 | Grosch et al. |
| 6,815,552 B2 | 11/2004 | Strebelle et al. |
| 2004/0068127 A1 | 4/2004 | Schoebrechts et al. |

FOREIGN PATENT DOCUMENTS

| DE | 196 23 611 | 12/1997 |
| EP | 0 526 945 | 2/1993 |
| EP | 0 549 013 | 6/1993 |
| EP | 0 709 339 | 5/1996 |
| EP | 0 819 683 | 1/1998 |
| WO | 99/14208 | 3/1999 |
| WO | 99/48883 | 9/1999 |

*Primary Examiner*—Bernard Dentz
(74) *Attorney, Agent, or Firm*—Oblon, Spivak, McClelland, Maier & Neustadt, P.C.

(57) ABSTRACT

A plant for producing hydrogen peroxide and using the hydrogen peroxide so made for manufacturing an oxirane by reaction between an olefin and said hydrogen peroxide, wherein the hydrogen peroxide is manufactured by an alkylanthrahydroquinone (AO) process in which an aqueous hydrogen peroxide solution is obtained by extraction, with substantially pure water, of a mixture derived from the oxidation of at least one alkylanthrahydroquinone, without a subsequent washing, purification treatment or combination thereof.

26 Claims, No Drawings

PROCESS FOR MANUFACTURING AN OXIRANE

The invention relates to a process for manufacturing an oxirane by reaction between an olefin and hydrogen peroxide in the presence of a catalyst and a diluent. The invention relates more particularly to a process for manufacturing 1,2-epoxypropane (or propylene oxide) by reaction between propylene and hydrogen peroxide.

It is known practice to manufacture propylene oxide by epoxidizing propylene using hydrogen peroxide in the presence of a catalyst of TS-1 type, as disclosed, for example, in patent application EP-A-0 230 949.

The hydrogen peroxide used is generally greatly freed from organic impurities. Thus, crude solutions of hydrogen peroxide ($H_2O_2$) arising from the extraction of a mixture derived from the oxidation of at least one alkylanthrahydroquinone, generally undergo one or more washing, extraction and/or distillation steps before being sold and/or used in synthetic processes. This is especially the case for the $H_2O_2$ solutions used for the manufacture of oxiranes.

Patent application EP-A-0 549 013 relates to an integrated process for oxidizing organic substrates and for producing $H_2O_2$ via an alkylanthraquinone (AO) process, which uses the water/alcohol mixture used during the oxidation of the organic substrate as the solvent for extracting the $H_2O_2$ from the quinone shuttle. The Applicant has found that this process has several drawbacks:

- the lack of flexibility of the overall process due to the interdependence of each step of the synthesis (AO and oxidation);
- the limitation or the alcohol content of the water/alcohol mixtures imposed by the extraction conditions, which penalizes the degree of conversion of the $H_2O_2$ during the epoxidation reaction;
- the difficulties of phase separation during extraction with a water/alcohol mixture;
- the passage of large amounts of methanol into the quinone shuttle, which, given the low flash point of methanol, results in an appreciable risk of explosion in the vapour phase during the step from oxidation to the synthesis of the $H_2O_2$;
- a large amount of quinones extracted in the water/alcohol mixture, which penalizes the economic viability of an industrial plant; and
- the pollution of the quinone shuttle by by-products of the oxidation reaction.

Moreover, the propylene used in the known epoxidation reactions is generally of relatively high purity, especially to avoid spurious oxidation reactions of the impurities, and mainly for reasons of yield and safety. Specifically, propane is the main impurity in propylene and it is reported in patent BE-A-1 001 884 that, in the presence of TS-1, hydrogen peroxide can oxidize an alkane.

In addition, in the case of propane, the oxidation product resulting therefrom is isopropanol. In the light of patent BE-A-1 001 884, a person skilled in the art would have deduced that, in a continuous process for producing propylene oxide with recycling of the organic reaction diluent (generally methanol), and/or in a continuous or batchwise process using a propane-rich source of propylene, isopropanol would accumulate in the diluent and end up being converted into acetone, which is generally difficult to separate from this diluent. In the presence of hydrogen peroxide, this acetone can form peroxides that are explosive and also insoluble in organic medium, which further increases the explosion hazard following their precipitation. This type of reasoning is applicable to any alkane oxidized in the presence of a peroxide compound an TS-1 and thus, to any source of olefin (recycled or otherwise) which is rich in alkane(s) and which would be intended for use in an epoxidation reaction.

Thus, patents U.S. Pat. Nos. 5,599,955 and 5,599,956 disclose the use of a substantially pure propylene, i.e. a propylene with a purity of at least 90% and preferably of at least 98%, the main impurity of which is propane.

Now, the various processes for synthesizing propylene (and olefins in general) generally lead to a propane content (or more generally a content of alkane(s)) which is appreciable, or even greater than that of the propylene, thus involving suitable separation and/or purification processes. Patents U.S. Pat. Nos. 5,599,955 and 5,599,956 mentioned above illustrate this problem.

In addition, various industrial processes using an olefin recycle the unconverted fraction thereof, which is conventionally enriched in alkane(s). These processes are thus also liable to require a separation of the constituents prior to this recycling. Examples of such processes are the polymerization of olefins and their epoxidation.

A subject of the present invention is a process for manufacturing an oxirane which avoids at least one of the abovementioned drawbacks, while at the same time having an increased degree of conversion and better selectivity than that obtained using a purified extract.

The invention consequently relates to a process for manufacturing an oxirane by reaction between an olefin and hydrogen peroxide in the presence of a catalyst and an organic diluent, according to which the hydrogen peroxide is an aqueous hydrogen peroxide solution obtained by extraction, with substantially pure water, of the mixture derived from the oxidation of at least one alkylanthrahydroquinone, without subsequent washing and/or purification treatment.

Specifically, the Applicant has found, surprisingly, that the fact of using for the epoxidation reaction an $H_2O_2$ solution extracted with water rather than with a water/alcohol mixture allows the degree of conversion of this $H_2O_2$ to be increased. In addition, the fact of using an unpurified extract allows a gain in selectivity compared with the use of a purified extract.

The processes for producing hydrogen peroxide using alkylanthraquinone(s), or AO processes, are well known and are widely documented in the literature (see, for example, "Ullmann's Encyclopedia of Industrial Chemistry, Fifth Edition, 1989, Volume 3, p. 447-57"). They consist in subjecting a working solution of at least one alkylanthraquinone and/or of at least one tetrahydroalkylanthraquinone to a hydrogenation step, in a diluent, to produce one or more alkylanthrahydroquinones and/or alkyltetrahydroanthrahydroquinones. The working solution leaving the hydrogenation step is then subjected to an oxidation with oxygen, air or oxygen-enriched air to give hydrogen peroxide and to reform the alkylanthraquinones and/or alkyltetrahydroanthraquinones. The hydrogen peroxide formed is then separated from the working solution by means of an extraction step. According to the present invention, this extraction is carried out using substantially pure water. The working solution leaving the extraction step is then recycled into the hydrogenation step in order to recommence the hydrogen peroxide production cycle.

The term "alkylanthraquinones" is intended to denote, for example, 9,10-anthraquinones substituted with at least one alkyl side chain of linear or branched aliphatic type comprising at least one carbon atom. These alkyl chains usually comprise less than 9 carbon atoms and preferably less than 6 carbon atoms. Examples of such alkylanthraquinones are 2-ethylanthraquinone, 2-isopropylanthraquinone, 2-sec- and 2-tert-butylanthraquinone, 1,3-, 2,3-, 1,4- and 2,7-dimethethylanthraquinone 2-iso- and 2-tert-amylanthraquinone, and mixtures of these quinones.

The expression "substantially pure water" is intended to denote a water containing less than 3% by weight of organic diluents, in particular of alcohol(s), preferably less than 0.1% or even less than 0.001% of these diluents. However, the extraction water may advantageously contain inorganic substances in a proportion of 0.001% by weight minimum, preferably 0.005% or even 0.01% minimum. However, the content of inorganic substances will not exceed 1% by weight, preferably 0.5%, or even 0.1%. These inorganic substances are advantageously substances which have a pH-regulating effect, such as acids and in particular strong acids such as nitric acid or phosphoric acid, or salts of such acids. These inorganic substances can also advantageously be substances which have an $H_2O_2$-stabilizing effect, such as alkali metal salts and alkaline-earth metal salts, and in particular sodium salts, such as sodium pyrophosphate. The extraction solution may thus comprise metal cations (such as alkali metals or alkaline-earth metals, for instance sodium) and/or anions such as phosphates, nitrates, etc. in low contents, generally less than 10 g/l, but greater than 0.01 g/l.

The $H_2O_2$ solution derived from the extraction, or crude $H_2O_2$ solution, generally contains less than 50% by weight of $H_2O_2$, usually less than 40% of $H_2O_2$. It generally contains more than 5% by weight of $H_2O_2$, usually more than 10%, in particular more than 20%, or even more than 30%. It does not undergo any subsequent washing and/or purification treatment before being used in the epoxidation reaction. Consequently, it contains organic impurities (products of degradation of the quinone shuttle) and inorganic impurities (cations and anions introduced by the extraction water, as well as those already preset in the mixture derived from the oxidation of the a alkylanthrahydroquinone(s)). The solution derived from the extraction may thus comprise organic impurities expressed as TOC (total organic carbon concentration), defined according to ISO standard 8245, in a proportion of at least 0.001 g/l, or even at least 0.01 g/l, or even at least 0.1 g/l, but not more than 10 g/l, or even 1 g/l, or even 0.2 g/l. It may also contain metal cations (such as alkali metals or alkaline-earth metals, for instance sodium) and/or anions such as phosphates, nitrates, etc. in low contents, generally less than or equal to 10 g/l, but greater than or equal to 0.01 g/l.

Before being used in the epoxidation reaction, the crude $H_2O_2$ solution may be diluted with water or any other solvent or liquid diluent which has no adverse effect on the epoxidation reaction. In general, the aqueous solution used for the epoxidation contains at least 5% by weight, usually at least 10% by weight, of $H_2O_2$, in particular at least 20% by weight. It usually contains not more than 50% by weight of peroxide compound, in particular 40% by weight.

The oxirane which may be prepared by the process according to the invention is an organic compound comprising a group corresponding to the general formula:

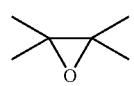

The oxirane generally contains from 3 to 10 carbon atoms, preferably from 3 to 6 carbon atoms. An oxirane which may be prepared advantageously by the process according to the invention is 1,2-epoxypropane.

The olefins which are suitable in the process according to the invention generally contain from 3 to 10 carbon atoms and preferably 3 to 6 carbon atoms. Propylene and butylene are particularly suitable. Propylene is preferred.

The catalysts used in the process according to the invention advantageously contain a zeolite, i.e. a solid containing silica which has a microporous crystal structure. The zeolite is advantageously free of aluminium. It preferably contains titanium.

The zeolite which may be used in the process according to the invention may have a crystal structure of ZSM-5, ZSM-11 or MCM-41 type or of beta-zeolite type. Zeolites of ZSM-5 type are suitable. Those with an infrared adsorption band at about 950-960 cm$^{-1}$ are preferred.

The zeolites which are particularly suitable are the titanium silicalites. Those corresponding to the formula $xTiO_2$ $(1-x)SiO_2$ in which x is from 0.0001 to 0.5, preferably from 0.001 to 0.05, have good performance qualities. Materials of this type, known under the name TS-1 and having a crystal structure of ZSM-5 type, give particularly favourable results.

The reaction medium according to the invention generally comprises a liquid phase and a gaseous phase.

The organic diluents which may be used in the process according to the invention may be organic derivatives such as aliphatic alcohols, containing from 1 to 4 carbon atoms. Methanol may be mentioned by way of example. The content of diluent in the liquid phase of the reaction medium is advantageously greater than 35% by weight, preferably greater than 60%, or even 75%. However, the content of diluent in the liquid phase of the reaction medium is generally less than 99% by weight, preferably less than 95%.

In one preferred variant of the process according to the invention, the oxirane produced in the reaction medium may be separated out by liquid-liquid extraction with a solvent as disclosed in patent application WO 99/14208 in the name of the Applicant.

The process according to the invention may be continuous or batchwise. If it is continuous, the unreacted olefin man be recycled into the reactor.

The reactor in which the process according to the invention takes place may be fed with a solution arising directly from the aqueous extraction step of an AO process. In this case, the plant in which the process according to the invention takes place also incorporates a plant for manufacturing the $H_2O_2$ solution according to an AO process. Such a plant and a process using it also constitute a subject of the present invention.

Alternatively, the solution may be stored and/or conveyed before being fed into the reactor, which is the case for the purified solutions currently used.

In the process according to the invention, a gas which has no adverse effect on the epoxidation reaction may also be fed into the reactor. Specifically, in patent application WO 99/48883, the Applicant has found that by introducing a gaseous compound into the reaction medium at a flow rate which is sufficient to enable the oxirane produced to be entrained and removed from the reactor at the same time as the gaseous compound, the contact time between the oxirane produced and the epoxidation reaction medium is reduced. This thus avoids the formation of by-products and increases the selectivity of the epoxidation.

One advantageous embodiment of the process according to the invention consists in introducing the gaseous phase into the reactor at a flow rate such that it not only entrains at least some of the oxirane produced, but also circulates the liquid phase in the reactor, in particular when this reactor is a reactor of loop type. In this case, the gaseous phase is generally introduced into the reactor at a flow rate such that the molar ratio of the flow rate of this gaseous phase to the $H_2O_2$ feed rate is at least 5, in particular at least 8, values of at least 10 being common. The molar ratio of these flow rates is generally less than or equal to 100, in particular less than or equal to 60, values of less than or equal to 40, or even 20, being common.

Any type of reactor may be used in the process according to the invention, in particular a reactor of loop type. Reactors of loop type with a bubble siphon, in which the circulation of the liquid and also optionally of the catalyst is obtained by bubbling a gas into one of the branches, are suitable. This type of reactor is disclosed in the abovementioned patent application WO 99/48883.

In the process according to the invention, it may prove to be advantageous to maintain the pH of the liquid phase during the reaction between the olefin and the $H_2O_2$ at a value of at least 4.8, in particular of at least 5. The pH is advantageously less than or equal to 6.5, in particular less than or equal to 6. Good results are obtained when the pH is from 4.8 to 6.5, preferably from 5 to 6. The pH of the liquid phase during the epoxidation reaction may be controlled by adding a base. This base may be chosen from water-soluble bases. They may be strong bases. Examples of strong bases which may be mentioned are NaOH and KOH. They may also be weak bases. The weak bases may be inorganic. Examples of weak inorganic bases which may be mentioned are $NH_4OH$, $Na_2CO_3$, $NaHCO_3$, $Na_2HPO_4$, $K_2CO_3$, $Li_2CO_3$, $KHCO_3$, $LiHCO_3$ and $K_2HPO_4$. The weak bases may also be organic. Weak organic bases which may be suitable are the alkali metal or alkaline-earth metal salts of carboxylic acids preferably containing from 1 to 10 carbon atoms. Sodium acetate may be mentioned by way of example. Weak bases give good results. Weak organic bases are preferred. Sodium acetate is particularly suitable.

The molar ratio between the amount of olefin used and the amount of $H_2O_2$ used is generally greater than or equal to 0.1, in particular greater than or equal to 1; and preferably greater than 5. This molar ratio is usually less than or equal to 100, in particular less than or equal to 50 and preferably less it than or equal to 25.

In the process according to the invention, when it is performed continuously and in the presence of a zeolite, the $H_2O_2$ is generally used in an amount of at least 0.005 mol per hour and per gram of zeolite, in particular of at least 0.01 mol per hour and per gram of zeolite. The amount of $H_2O_2$ is usually less than or equal to 2.5 mol per hour and per gram of zeolite, and in particular less than or equal to 1 mol per hour and per gram of zeolite. Preference is shown for an amount of $H_2O_2$ of greater than or equal to 0.03 mol per hour and per gram of zeolite and less than or equal to 0.1 mol per hour and per gram of zeolite.

The reaction between the olefin and the $H_2O_2$ may be carried out in the presence of a salt such as a metal salt or an ammonium salt. The metal may be chosen from alkali metals and alkaline-earth metals such as lithium, sodium, potassium, caesium, magnesium, calcium, strontium and barium. The metal salts are advantageously halides, oxides, hydroxides, carbonates, sulphates and phosphates and organic acid salts such as acetates. The halides are generally fluorides, chlorides, bromides and iodides. Preference is shown for chlorides. The salt advantageously used in the process according to the present invention is preferably an alkali metal halide and advantageously sodium chloride. The amount of metal salt used is expressed as the content of metal ions or of ammonium ions arising from the salt relative to the amount of catalyst expressed in millimoles (mmol) of metal or of ammonium per gram of zeolite. This content may be greater than or equal to $10^{-4}$ mmol/g of zeolite and less than or equal to 10 mmol/g of zeolite. Advantageously, the metal salt content is greater than or equal to $10^{-3}$ mmol/g of zeolite and less than or equal to 1 mmol/g of zeolite. Preference is shown for a content of greater than or equal to $10^{-2}$ mmol/g of zeolite and less than or equal to 0.5 mmol/g of zeolite.

The temperature of the reaction between the olefin and the $H_2O_2$ is advantageously greater than 35° C. to overcome the gradual deactivation of the catalyst. It is advantageous to perform the reaction at temperature of greater than or equal to 40° C. and preferred greater than or equal to 45° C. A temperature of greater than or equal to 50° C. is most particularly preferred. However, the reaction temperature is generally less than 100° C. and preferably less than 80° C. The temperature at which the olefin reacts with the $H_2O_2$ is generally between 40° C. and 100° C. and preferably between 45° C. and 80° C.

In the process according to the invention, the reaction between the olefin and the $H_2O_2$ may take place at atmospheric pressure. It may also take place under pressure. Generally, this pressure does not exceed 40 bar. A pressure of 20 bar is suitable in practice.

According to one particularly advantageous variant of the process according to the invention, the olefin is reacted with the hydrogen peroxide in the is presence of the catalyst and the organic diluent in a reactor in the liquid phase which is fed with hydrogen peroxide and organic diluent as well as with a fluid comprising the olefin and at least 10% by volume of alkane(s). The alkane content in the fluid is preferably greater than 10% by volume.

This variant is advantageous since it upgrades the various sources of olefins not freed of alkanes by using them to manufacture oxiranes, and since it reduces, surprisingly, during an oxidation reaction of an alkane with a hydrogen peroxide, the production of alcohol and of ketone in the presence of an olefin, this even taking account of the dilution factor.

Consequently, the danger of precipitation of explosive peroxides is markedly less than that which would be theoretically expected and can consequently be managed with ease in a plant of industrial size.

One Of the essential advantages of the advantageous variant lies in feeding a fluid containing at least 10% by volume of one or more alkane(s) into the reactor. The content of alkane(s) in this fluid may in certain cases be at least equal to 20% by volume, or even 30%. Fluids containing at least 50% by volume of alkane(s) may also be used. However, it is not recommended to use fluids containing more than 95% by volume of alkane(s), and it is even preferable to use fluids not containing more than 85% alkane(s).

The fluid usually contains more than 50% by volume of olefin, in particular at least 60% by volume and preferably at least 70% by volume. The amount of hydrogen introduced into the epoxidation reactor is usually less than 5% of the volume of the fluid, and is preferably equal to 0%. The amount of oxygen introduced into the epoxidation reactor is generally less than 10% of the volume of the fluid.

The alkane(s) contained in the fluid according to the present invention generally contain(s) from 3 to 10 carbon atoms and preferably 3 to 6 carbon atoms. Preferably, the alkane is linear and does not contain any aromatic substitutents in particular. When the olefin according to the invention is propylene, the alkane(s) consist(s) mainly of propane. Preferably, the alkane is not used as organic diluent for the epoxidation reaction and is different from the organic diluent.

The process according to the advantageous variant may be continuous or batchwise. If it is continuous, the fluid may be recycled into the reactor after the reaction between the olefin and the hydrogen peroxide.

In a first case of the advantageous variant of the process according to the invention, the process is continuous and the fluid fed into the reactor during the start of the process contains less than 10% by volume of alkane(s). During the process, the fluid is recycled into the reactor after the reaction between the olefin and the hydrogen peroxide such that the fluid recycled is gradually enriched with alkane. The alkane content in the fluid thus reaches a value of at least 10% by volume.

In a second case of the advantageous variant of the process according to the invention, this process is continuous or batchwise and the fluid fed into the reactor during the start of the process already contains at least 10% by volume of alkane(s).

Preferably, the fluid (comprising the olefin and the alkane (s)) which is fed into the reactor is a gas. In this case, one particular embodiment of the advantageous variant of the process according to the invention consists in introducing this gas into the reactor at a flow rate such that it not only entrains at least some of the oxirane produced, but also circulates the liquid phase in the reactor, in particular when this reactor is a reactor of loop type. In this case, the gas is generally introduced into the reactor at a flow rate such that the molar ratio of the flow rate of this gas to the feed rate of the peroxide compound is at least 5, in particular at least 8, values of at least 10 being common. The molar ratio of these flow rates is generally less than or equal to 100, in particular less than or equal to 60, values of less than or equal to 40, or even 20, being common.

In the advantageous variant of the process according to the invention, when it is performed continuously, preference is shown for an amount of hydrogen peroxide of greater than or equal to 0.03 mol per hour and per gram of zeolite and less than or equal to 0.25 mol per hour and per gram of zeolite.

In the advantageous variant of the process according to the invention, the aqueous hydrogen peroxide solution usually contains not more than 70% by weight of peroxide compound, in particular 50% by weight.

The invention also relates to a process for manufacturing an oxirane, according to which an olefin is reacted, in a reactor in the liquid phase, with hydrogen peroxide in the presence of a catalyst and an organic diluent, in which the reactor is fed with hydrogen peroxide and with organic diluent, as well as with a fluid comprising the olefin and at last 10% by volume of alkane(s).

This other process of the invention corresponds to the advantageous variant disclosed above when it is performed as such without being combined with the first process of the invention which uses an aqueous hydrogen peroxide solution obtained by extraction, using substantially pure water, of the mixture derived from the oxidation of at least one alkylanthrahydroquinone, without subsequent washing and/or purification treatment.

The conditions under which this other process may be performed are identical to those of the first process except for the use of a crude hydrogen peroxide solution.

EXAMPLE 1 (ACCORDING TO THE INVENTION) AND EXAMPLE 2C (COMPARATIVE)

A continuous reactor containing 5.25 g of TS-1 is maintained at 35° C. and at atmospheric pressure and fed with 0.57 mol of $H_2O_2$/h, introduced in the form of an aqueous 40 wt % solution, with 4.75 mol of methanol/h and with 250 Nl/l (i.e. 11.2 mol/h) of propylene. The liquid and gaseous phases leaving are analysed to determine the proportions of the various organic products and also the degree of conversion of the $H_2O_2$.

The table below summarizes the results obtained after the tests, starting with a fresh TS-1 catalyst prepared according to the procedures known in the literature.

| Example No. | 1 (invention) Crude extraction $H_2O_2$ | 2C (comparison) Purified $H_2O_2$ |
|---|---|---|
| Degree of conversion of the $H_2O_2$ after running for 2 h | 76.7 | 76.0 |
| Idem after 6 h | 54 | 53 |
| Selectivity* after 6 h | 90.5 | 85.4 |

*the selectivity is expressed by the ratio mol/mol PO (propylene oxide) formed/total of organic products formed.

As is known, a gradual loss of activity of the catalyst is observed, which is not affected by the quality of $H_2O_2$ used. Only the selectivity is favourably influenced in the presence of the crude $H_2O_2$.

The respective contents of anions and cations in these $H_2O_2$ solutions should be noted:

| Content in mg/l | Crude $H_2O_2$ | Purified $H_2O_2$ |
|---|---|---|
| Na | 26 | 2.3 |
| Other cations (except $H^+$) | <0.3 | <0.3 |
| $NO_3$ | 34 | 3.7 |
| Phosphates expressed as P | 28 | 1.4 |
| TOC | 172 | 69 |

EXAMPLE 3 (ACCORDING TO THE INVENTION) AND EXAMPLE 4C (COMPARATIVE)

The table below summarizes tests that are identical in all respects to Example 1 and Example 2C, during a following cycle after regeneration of the catalyst. This regeneration is obtained by passing air heated to 300° C. over the catalyst for 7 h.

| Example No. | 3 (invention) Crude $H_2O_2$ | 4C (comparison) Purified $H_2O_2$ |
|---|---|---|
| Degree of conversion of the $H_2O_2$ after running for 2 h | 75.4 | 75.6 |
| Idem after 6 h | 53.5 | 54.3 |
| Selectivity** after 6 h | 91.1 | 85.7 |

It is confirmed that the activities have, to within the accuracy of the measurements, remained identical and that the difference in selectivity is maintained.

EXAMPLE 5C (COMPARATIVE) AND EXAMPLE 6 (ACCORDING TO THE INVENTION)

An $H_2O_2$ synthesis solution obtained after oxidizing a quinones/hydroquinones shuttle was extracted using a methanol/water mixture containing 52% by weight of methanol. This aqueous extract was then used in a propylene epoxidation test (Example 5C) and the performance qualities obtained were compared with those of a similar test carried out with crude $H_2O_2$ at 40% by weight in water, obtained from the extraction of the same shuttle with substantially pure water (Example 6). This shuttle contains 11.8 g/kg of $H_2O_2$.

The extraction with the water/alcohol mixture was carried out in 4 steps:

A first extraction was carried out by treating 14 331 g of shuttle (containing 169.1 g of $H_2O_2$ in total) with 1511 g of the methanol/water mixture. The methanol/water phase is denser than the starting organic solution and separates out relatively quickly (in about 15 min) to give 1085 g of extract. Its $H_2O_2$ concentration, determined by iodometry, is equal to 3.18 mol $H_2O_2$/kg, which corresponds to 3.45 mol or 117.4 g of $H_2O_2$ (=69% of the total present).

A second extraction was carried out with 1522 g of the same methanol/water mixture. The separation is less sharp. The separation of the phases is fairly slow: more than 1 h is required to be able to separate the phases. In contrast with the first extraction, the methanol/water phase is less dense this time and consists of 1215 g of extract. Its $H_2O_2$ concentration is equal to 0.833 mol/kg, which is equivalent to 1.012 mol or 34.4 g of $H_2O_2$. 90% of the total $H_2O_2$ are thus recovered in two extractions.

A third extraction was carried out with 1511 g of the same methanol/water mixture. The same separation difficulty was encountered, with recovery of about 1446 g a methanol/water phase. Its $H_2O_2$ concentration is equal to 0.244 mol/kg, which is equivalent to. 0.353 mol or 12.0 g of $H_2O_2$ (i.e. 96.9% of the total $H_2O_2$ in 3 extractions).

Finally, a fourth extraction was carried out with 1517 g of the same methanol/water mixture. The same separation difficulty was encountered, with recovery of about 1497 g of methanol/water phase. Its $H_2O_2$ concentration is equal to 0.071 mol/kg, which is equivalent to 0.106 mol or 3.6 g of $H_2O_2$ (i.e. 99.0% of the total $H_2O_2$ in 4 extractions).

The 4 extracts were then mixed together, to give a methanol/water solution containing 0.94 mol $H_2O_2$/kg (effectively confirmed by titration). The methanol content determined by GC is in the region of 437 g/kg.

The content of "useful" quinones (=which may be used to produce $H_2O_2$) lost in this phase is 0.020 g/kg of extract.

There has moreover clearly been passage of some of the methanol into the quinone shuttle, as demonstrated by the differences between the weights of the methanol/water mixtures used and those of the collected extracts (in particular for the first and second extractions). The methanol content of the quinone shuttle, determined by GC, is effectively in the region of 6.0% by weight.

The propylene (Pe) epoxidation tests were carried out in a plant of bubble siphon type under the following conditions: T: 55° C.; flow rate of Pe: 75 Nl/h; $H_2O_2$: 0.17 mol $H_2O_2$/h; concentration of $H_2O_2$ in the zero-conversion loop: 1.0 mol/kg; catalyst: 0.53 g of TS-1.

As regards Example 5, the introduction of the mixture alone of the four methanol/water extracts containing $H_2O_2$ into the bubble siphon plant would lead, following stripping, to a methanol-poor medium (conc. <440 g/kg. Consequently, additional methanol was added so as to keep it concentration in the loop at ≈440 g/kg which corresponds to the methanol content of the reference test with crude $H_2O_2$ (Example 6).

The results obtained are given in the table below:

|        | Degree of conversion of the $H_2O_2$ (%) | | | | | | | | |
|--------|------|------|------|------|------|------|------|------|------|
|        | 2 h  | 3 h  | 4 h  | 5 h  | 6 h  | 7 h  | 24 h | 25 h | 26 h |
| Ex. 5C | 30.4 | 20.7 | 18.6 | 15.3 | 12.6 | 10.4 | 8.7  | 8.4  | 8.1  |
| Ex. 6  | 33.3 | 25.5 | 24.4 | 20.4 | 20.1 | 19.6 | 17.5 | 18.4 | 17.2 |

EXAMPLES 7 TO 9

Propylene oxide was manufactured in a bubble siphon reactor as disclosed in patent application WO 99/48883, by reaction between propylene and hydrogen peroxide in the presence of methanol and of catalyst TS-1 used in the form of beads 0.5 mm in diameter.

The tests were carried out at a temperature of 55° C., with a continuous feed of hydrogen peroxide at a flow rate of 0.17 mol/h. The total flow rate of gas is 75 Nl/h (i.e. 3.3 mol/h). The initial $H_2O_2$ concentration in the zero-conversion loop was 1.5 mol/kg. The amount of catalyst used was 4.5 g of beads containing 1.5 g of TS-1.

In Example 1, a mixture containing 75% "polymer-grade" propylene (98% propylene and 0.3% propane) and 25% propane (molar %) was used; in Example 2, 100% "polymer grade" propylene was used, and in Example 3, a mixture containing 75% "polymer grade" propylene and 25% nitrogen was used.

The results obtained are given in the table below.

The selectivity towards propylene oxide is given by the molar ratio, expressed as a percentage, between the amount of propylene oxide obtained divided by the sum of all the C3 organic products formed.

|           | Degree of conversion of $H_2O_2$ (%) | | | Selectivity |
|-----------|------|------|------|------|
|           | 5 h  | 6 h  | 7 h  | 5 h  |
| Example 7 | 57.4 | 55.3 | 52.6 | 85.8 |
| Example 8 | 67.2 | 64.0 | 61.7 | 84.5 |
| Example 9 | 59.1 | 53.3 | 51.2 | 85.9 |

The isopropanol production measured after 5 h is 0.007 mmol/h for Example 1. There is no detectable trace of isopropanol in Tests 2 and 3.

EXAMPLE 10

A test under conditions identical to those of Examples 7 to 9 above was carried out with pure propane. The isopropanol production measured after 5 h is 0.11 mmol/h, i.e. a factor of 16 relative to Example 1. There is also formation of 0.04 mmol/h of acetone. The $H_2O_2$ conversion is very low, i.e. 1% after 5 h.

This application is a Divisional of U.S. application Ser. No. 10/940,992, filed Sep. 15, 2004, now allowed; which is a Divisional of U.S. application Ser. No. 10/182,776, now U.S. Pat. No. 6,815,552; which is a National Stage application of PCT/EP01/00976 filed Jan. 30, 2001. In addition, priority to European Application 00200344.0, filed Feb. 2, 2000, is claimed.

The invention claimed is:

1. A plant for producing hydrogen peroxide and using the hydrogen peroxide so made for manufacturing an oxirane by reaction between an olefin and said hydrogen peroxide,
wherein the hydrogen peroxide is manufactured by an alkylanthrahydroquinone (AO) process in which an aqueous hydrogen peroxide solution is obtained by extraction, with substantially pure water, of a mixture derived from the oxidation of at least one alkylanthrahydroquinone, without a subsequent washing, purification treatment or combination thereof.

2. The plant according to claim 1, wherein the oxirane is 1,2-epoxypropane and the olefin is propylene.

3. The plant according to claim 1, wherein the substantially pure water comprises less than 3% by weight of organic diluents.

4. The plant according to claim 1, wherein the hydrogen peroxide solution obtained by extraction comprises at least 0.001 g/l and not more than 10 g/l of organic impurities expressed as TOC.

5. The plant according to claim 1, wherein the hydrogen peroxide solution obtained by extraction comprises metal cations and anions in an amount of greater than or equal to 0.01 g/l and less than or equal to 10 g/l.

6. The plant according to claim 1, wherein the hydrogen peroxide solution obtained by extraction comprises at least 5% by weight and not more than 500 by weight of hydrogen peroxide.

7. The plant according to claim 1, wherein said reaction between an olefin and said hydrogen peroxide is performed in the presence of a catalyst and an organic diluent, wherein said catalyst is titanium silicalite with a crystal structure of ZSM-5, and the diluent is methanol.

8. The plant according to claim 1, wherein said reaction between an olefin and said hydrogen peroxide is performed in the presence of a catalyst and an organic diluent, wherein a liquid phase and a gaseous phase are present, and wherein the organic diluent is present in the liquid phase in an amount of greater than 350 by weight.

9. The plant according to claim 1, wherein the olefin is reacted with hydrogen peroxide in the presence of the catalyst and an organic diluent in a reactor in the liquid phase, wherein the reactor is fed with hydrogen peroxide, the organic diluent and a fluid comprising the olefin and at least 10% by volume of one or more alkanes.

10. The plant according to claim 9, wherein the one or more alkanes is present in the fluid in an amount of at least 20% by volume.

11. The plant according to claim 9, wherein the one or more alkanes is present in the fluid in an amount of less than or equal to 95% by volume.

12. The plant according to claim 9, further comprising
recycling the fluid into the reactor after reacting the olefin and hydrogen peroxide,
wherein the process is a continuous process, and
wherein the fluid initially fed into the reactor comprises less than 10% by volume of one or more alkanes, and after recycling the fluid into the reactor, the fluid is gradually enriched with the one or more alkanes until the one or more alkanes is present in an amount of at least 10% by volume.

13. The plant according to claim 9, wherein the fluid which initially feeds the reactor comprises one or more alkanes in an amount of at least 10% by volume.

14. The plant according to claim 9, wherein the reactor is a loop reactor, the fluid comprising the olefin and the one or more alkanes is a gas and the molar ratio of a flow rate of the gas to a feed rate of hydrogen peroxide is greater than or equal to 5.

15. The plant according to claim 9, wherein the oxirane is 1,2-epoxypropane, the olefin is propylene and the alkane is propane.

16. The plant according to claim 3, wherein the substantially pure water contains less than 3% by weight of one or more alcohols.

17. The plant according to claim 5, wherein the metal cations are alkali metals or alkaline earth metals.

18. The plant according to claim 17, wherein the metal is sodium.

19. The plant according to claim 5, wherein the anions are phosphates or nitrates.

20. The plant according to claim 7, wherein the titanium silicalite is a TS-1 silicalite.

21. The plant according to claim 10, wherein the one or more alkanes is present in the fluid in an amount of at least 30% by volume.

22. The plant according to claim 11, wherein the one or more alkanes is present in the fluid in an amount of 85% by volume.

23. The plant according to claim 14, wherein the molar ratio of the flow rate of the gas to the feed rate of hydrogen peroxide compound is greater than or equal to 10.

24. The plant according to claim 6, wherein the hydrogen peroxide solution obtained by extraction comprises more than 30% by weight and less than 50% by weight of hydrogen peroxide.

25. The plant according to claim 1, which is carried out without a subsequent purification treatment.

26. The plant according to claim 25, which is carried out without subsequent distillation treatment.

* * * * *